United States Patent [19]

Podolsky et al.

[11] Patent Number: 4,693,606

[45] Date of Patent: Sep. 15, 1987

[54] APPARATUS AND METHOD FOR MEASURING MUSCLE SARCOMERE LENGTH IN VIVO

[75] Inventors: Richard J. Podolsky, Washington, D.C.; Gordon R. Baker, Rockville, Md.; Bernhard Brenner, Tubingen, Fed. Rep. of Germany

[73] Assignee: The United States of America as represented by the Department of Health and Human Services, Washington, D.C.

[21] Appl. No.: 784,258

[22] Filed: Oct. 3, 1985

[51] Int. Cl.$^4$ ............................................. A61N 5/06
[52] U.S. Cl. .................................... 356/355; 128/774; 33/125 A
[58] Field of Search ..................... 356/354, 355, 356; 128/303 R, 303.1, 664, 665, 774; 350/162.11; 33/125 A

[56] References Cited

U.S. PATENT DOCUMENTS 4,570,641  2/1986  Lieber et al. ................... 356/355 X Primary Examiner—Eugene R. LaRoche
Assistant Examiner—Robert J. Pascal
Attorney, Agent, or Firm—Browdy and Neimark

[57] ABSTRACT

A laser diffraction apparatus for measuring muscle sarcomere length IN VIVO, primarily useful for tendon transfer procedures, includes a screen and laser assembly adapted to direct a laser beam through a muscle tissue supported by a 180° deflection prism towards the screen which receives the resultant diffraction pattern. This diffraction pattern determines the length of the muscle's sarcomere. A mechanism is provided for adjustably positioning the laser assembly and the 180° deflection muscle tissue supporting prism relative to the operative field.

16 Claims, 5 Drawing Figures

MUSCLE FIBER

APPARATUS AND METHOD FOR MEASURING MUSCLE SARCOMERE LENGTH IN VIVO

FIELD OF THE INVENTION

The present invention relates to an apparatus and method for measuring muscle sarcomere length in vivo, especially using laser diffraction.

BACKGROUND OF THE INVENTION

Adjustment of muscle length during tendon transfer procedures and tendon repairs is a necessary element in obtaining maximum force from the transferred muscle. A muscle that is set at a length different than the optimal muscle length will not be able to develop maximum force. Usually, surgeons rely on their own experience in determining the amount of tension for setting a muscle to its optimal muscle length, and it is not uncommon for the surgeon to overpull the muscle during the tendon transfer.

Adjustment of muscle length during tendon transfers has always presented a problem for the hand surgeon, because the force developed by an activated muscle is length-dependent. The objective of the surgeon in any muscle transfer should be to restore the transferred muscle to its optimal length. Previously guidelines for adjusting muscle length generally were based on total muscle excursion and the passive tension felt during surgery. The passive tension felt during surgery depends not only on the length of the muscle and inherent qualities of the individual muscle fibers, but also on the surrounding connective tissue adhesions.

While passive tension is important for the assumption of functional position, it is a poor predictor of muscle function. If the muscle is paralyzed or under tourniquet control, extrinsic factors are eliminated, and the muscle exerts passive tension but not active tension. Thus, methods for tendon transfer that depend on passive tension give no information on how the muscle will later function in the patient. Moreover, there are no accurate pratical clinical or physiologic guidelines for assuring that optimal muscle length is restored following tendon transfer procedures.

Over the years, much work has been done on the problem of restoring a muscle to its optimal muscle length during tendon transfer procedures. For example, in the publication of Omer et al, entitled "Determination of Physiologic Length of a Reconstructed Muscle-Tendon Unit Through Muscle Stimulation", published in the Journal of Bone Joint Surgery, Vol. 47, 1965, the determination was made that each muscle has an optimal length at which force is maximal, and the authors developed a procedure involving electrical stimulation of the muscle during surgery to estimate "ideal muscle resting tension". This method was improved upon over the years, but the procedure is still time consuming and complicated, and has not found wide surgical acceptance.

Furthermore, attempts have been made to set the sarcomere length (the portion of the striated muscle fibril lying between two adjacent Z dark lines, otherwise know as Krause's membranes) to a value that is close to the peak of the length-activated tension relation (adjusting the length of the muscle so that the active tension is at maximum with the body portion, e.g. wrist or hand, in the position of function). These attempts must include some accurate means for measuring the sarcomere length.

For example, the publication to Sandow, entitled "Diffraction Patterns of the Frog Sartorius and Sarcome Behavior Under Stretch", published in the Journal of Cell Compar. Physiol., Vol. 9, 1937, mentions employing an optical system for diffracting light through frog sartorius tissue and photographing the grating patterns of the regular alternation of transverse dark and light bands of the component muscle fibers. It was determined that a muscle may be a set of "superimposed gratings", as if the muscle were a singe grating whose grating element distance is the length of the sarcomere of the muscle (the length S of the sarcomeres in the diffracting segment can be determined by means of the grating equation: $n\lambda = S \sin\theta_n$, where n is the order of the spectrum; $\lambda$, the wave length of the light employed; and $\theta_n$ the angle of diffraction of the $n^{th}$ order spectrum). However, the Sandow apparatus used to determine sacromere characteristics by light diffraction does not utilize a laser or the like, is cumbersome, difficult to support tissue under examination, and lacks practicality.

The patent literature contains some examples of fiber measurement. Thus, the device of Troll et al (U.S. Pat. No. 3,659,950) measures fiber width rather than an axial spacing. The device of Hansler (U.S. Pat. No. 3,804,529) measures axial spacings that are large compared to a laser beam diameter and thus requires that the fiber be continuously moved relative to the laser beam to obtain a measurement. Patents which show laser measuring devices of various types include U.S. Pat. Nos. 3,518,007, Ito; 3,698,817, Iimura et al.; 3,858,981, Jaerisch et al; 3,664,739 Pryor; and 4,483,618, Hamar.

No method or apparatus for its practice has previously been available which incorporates the use of laser diffraction for the accurate determination of muscle sarcomere length IN VIVO, nor has there been a successful procedure for accurately restoring tendons during surgical transfers. Moreover, there is a great need for such an apparatus and method which will enable a surgeon to repair and restore muscles so that the muscles may have the ability to function at a maximum force in an awake patient.

SUMMARY OF THE INVENTION

Accordingly, it is an object of the present invention to overcome the deficiencies of the prior art, such as those set forth above.

It is a further object of the present invention to provide for accurately measuring muscles sarcomere lenght IN VIVO.

It is yet another object of present invention to provide a method and apparatus of employing laser diffraction or the like for the accurately measuring muscle sarcomere length IN VIVO.

It is still another object of the present invention to provide a method of employing laser diffraction for measuring sarcomere length so that tendons may be accurately replaced or restored whereby the tendons will function at a maximum force in the patient.

It is another object of the present invention to provide an apparatus employing laser diffraction or the like which will accurately indicate on a readout screen the muscle sarcomere length of a muscle segment.

It is still another object of the present invention to provide an apparatus employing laser diffraction or the like including a support means for resting muscle tissue thereon while under examination.

It is another object of the present invention to provide an apparatus employing laser diffraction which will be precise in measuring muscle sacromere length, easy to operate, and inexpensive to manufacture.

Still other objects, features and attendant advantages of the present invention will become apparent to those skilled in the art from a reading of the following detailed description of embodiments constructed in accordance therewith, taken in conjuction with the accompanying drawings.

DETAILED DESCRIPTION OF EMBODIMENTS

Figure 1A:
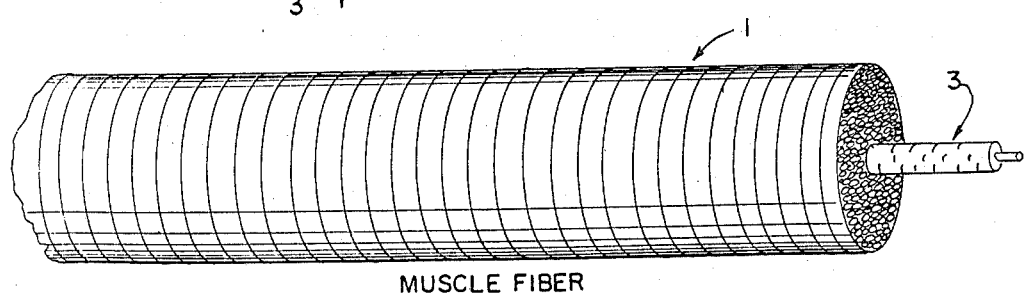
FIG. 1a is a perspective view simulating a muscle fiber for normal rabbit psoas muscle (adapted from H. E. HUXLEY, ENDEAVOUR, 15, 177, 1956)
Figure 1B:
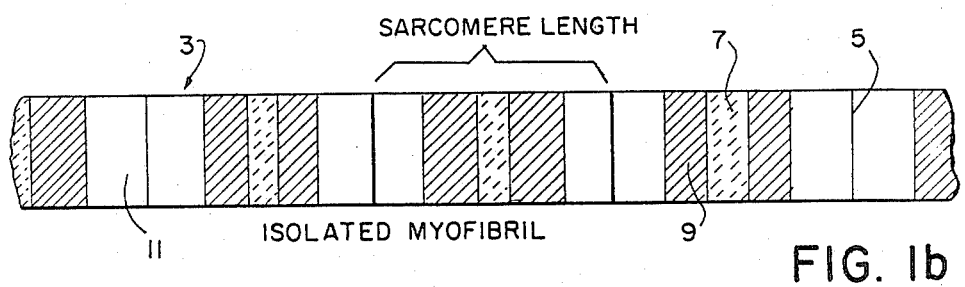
FIG. 1b is a schematic representational view showing the banded nature of an isolatied myofibril for normal rabbit psoas muscle (H. E. HUXLEY, ENDEAVOUR, 15, 177, 1956)

Reffering to FIG. 1a and FIG. 1b of the drawings, normal muscle fiber 1 from a striated muscle bundle is shown as having an exposed plurality of bunched fibrils 3. The fibrils 3 make up the muscle fibre 1 and internally extend along the entire muscle fibre's length. As best seen in FIG. 1b, an isolated myofibril is shown as having alternating transverse dark and light colored bands. The light colored bands 11 define the "I" bands and include an intermediate dark line 5 known as the "Z" line. Dark colored bands 9, called "A" bands, consist of an intermidate region 7 known as the "H" zone. The sarcomere length is defined as the region between two adjacent dark "Z" lines 5.

Typically, the sarcomere length is between 2 and 3 microns of micrometers ($\mu$ or $\mu$m; about 0.0001 inch), so that 300 to 500 individual sarcomeres are included in a 1 mm diameter laser beam.

The isolated myofibril 3, illustrated in FIG. 1b, shows the fibril at the resting position. If the fibril is in a contracted state, the "I" bands 11 and the "H" zone regions 7 are shortened, decreasing the sarcomere length. Furthermore, if the fibril 3 is in an extended state, the "I" bands 11 and the "H" zones 7 widen thereby increasing the sarcomere length. Accordingly, it is apparent that the sarcomere length is dependent upon the lenght of the "I" bands and the "H" zones at various fibril lengths (extended, rested and contracted).

APPARATUS

Figure 2:
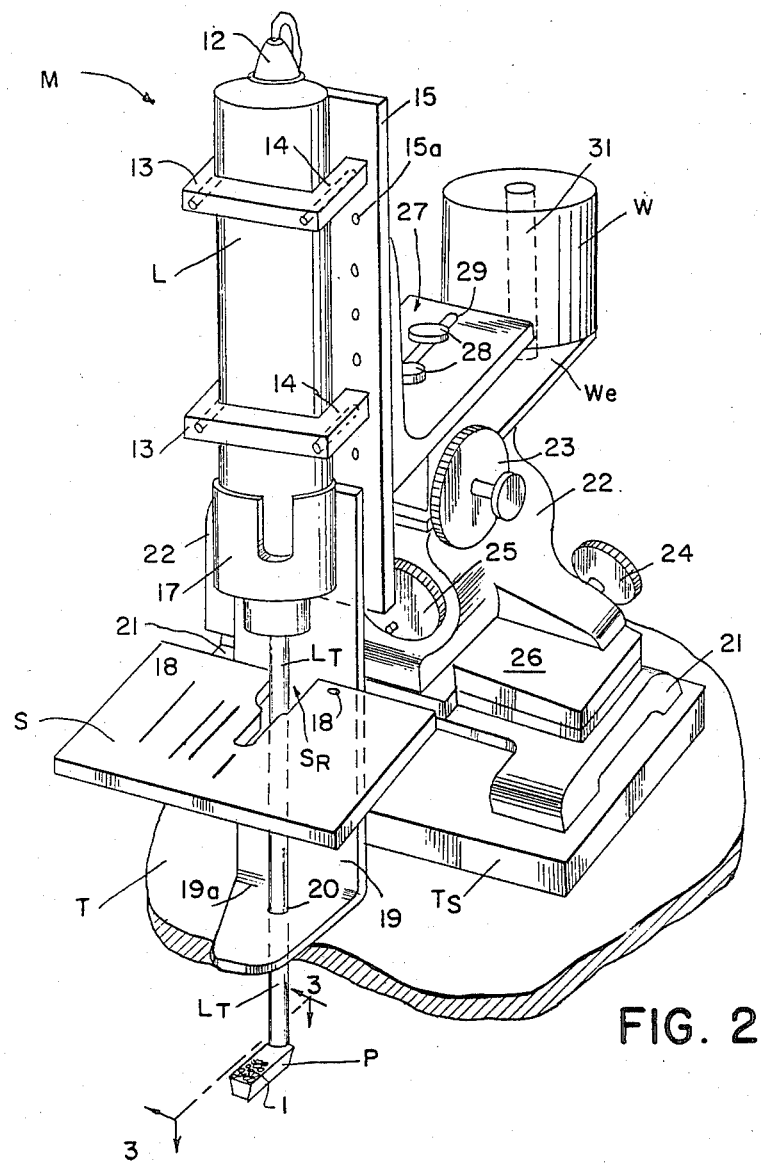
FIG. 2 is a perspective view of an embodiment of a muscle diffractometer apparatus in accordance with the present invention.

Referring to FIG. 2 of the drawings, an apparatus M corresponding to a preferred embodiment of the present invention is shown for measuring muscle sarcomere length IN SITU during tendon transfer procedures. The apparatus M includes a 2-mw helium-neon laser L ($\lambda = 6320$ Å, beam size 0.5 mm) connected to any suitable power source by means of plug 12. The laser L is vertically and adjustably mounted to an erect laser board 15 secured thereto by horizontally spaced U-shaped clamps 13 or other suitable means. Each clamp 13 is secured to the laser board 15 by means of elongated screws 14 or the like. The laser board 15 is provided with a plurality of spaced apart apertures for receiving the ends of clamps 13. It should be understood that clamps 13 may be positioned to support laser L anywhere along the vertical length of the laser board 15.

The base or bottom of the laser L is equipped with a light transmitting tube $L_T$ fastened to the laser L by means of a base sleeve 17. An L-shaped support member 19 is also vertically mounted to the laser board 15 for supporting a light screen S directly beneath the base sleeve 17 of the laser L. The screen S, of substantially rectangular configuration, is secured to the L-shaped support member 19 by means of screws or bolts 18 and is provided with a Y-shaped channel for the passage therethrough of the light transmitting tube $L_T$. The L-shaped support member 19 includes a normally extended region 19a equipped with an aperture 20 for receiving the light transmitting tube $L_T$ near its distal end which maintains the light transmitting tube $L_T$ in an erect vertical alignment with laser L.

The laser board 15 is mounted to an adjusting support 27 which acts to adjust the position of the laser assembly (laser L, screen S and light transmitting tube $L_T$) in any predetermined direction by means of adjustment screws/knobs 23, 24 and 25 (x, y and z axial adjustments). Adjusting support 27 is equipped with a slot 29 for receiving fulcrum pins 28, 28 which enable the laser assembly to be balanced with a weight W supported on a plate $W_P$ by means of a screw or bolt 31. The entire adjusting support 27 is mounted to a base housing 22 including a plurality of stationary block members 26 which are supported by base legs 21.

The entire apparatus M may be mounted to a table support $T_S$ for resting the apparatus M on a conventional support T, such as an operating room table or lab bench. It should be understood that the base housing 22 can be made of any rigid material, such as metal or hard plastic, as long as the housing 22 possesses sufficient rigidity and strength.

Figure 3:
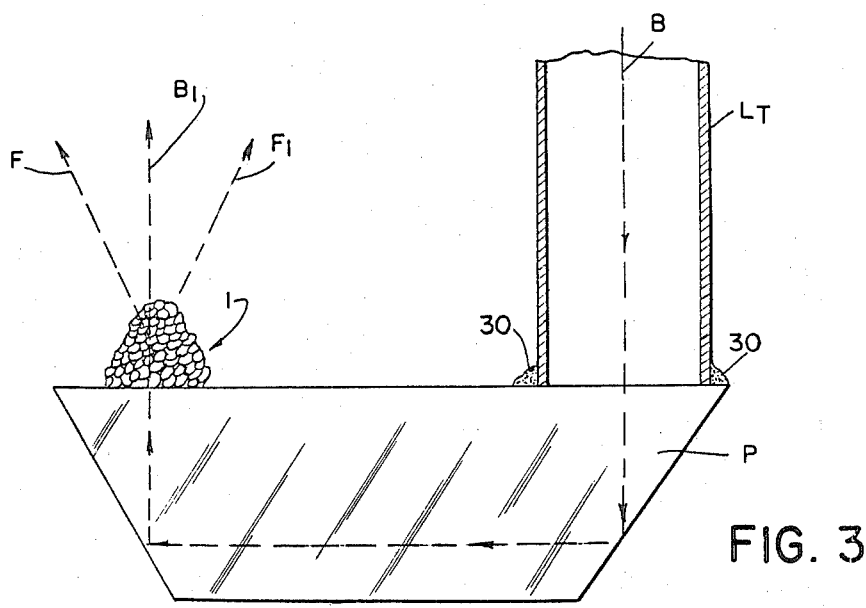
FIG. 3 is a cross-sectional view of the muscle support apparatus of the present invention taken along the line 3—3 in FIG. 2, broken lines illustrating the directional path of light beams.

As best seen in FIG. 3 of the drawings, a very small prismatic support P is provided to support muscle tissue 1 under examination for measurement of sarcomere length. The prismatic support P is positioned underneath the light transmitting tube $L_T$ in order to redirect the laser beam B (shown by broken lines) through the muscle tissue 1 and back toward the screen S (180° prism). As the laser beam B passes through muscle tissue 1 disposed on the surface of the prismatic support P, the beam B is diffracted upwardly and split into beams F, $B_1$, and $F_1$. The prism P is rigidly attached to the light transmitting tube $L_T$ by means of a suitable adhesive 30 or the like, which enables the free movement of the prism P and the tube $L_T$ as a unit in any direction or at any elevation relative to the operative field in conjunction with a patient (IN VIVO), and this arrangement isolates the interface between the transmitting tube $L_T$ and the prism P (shielding means).

Figure 4:
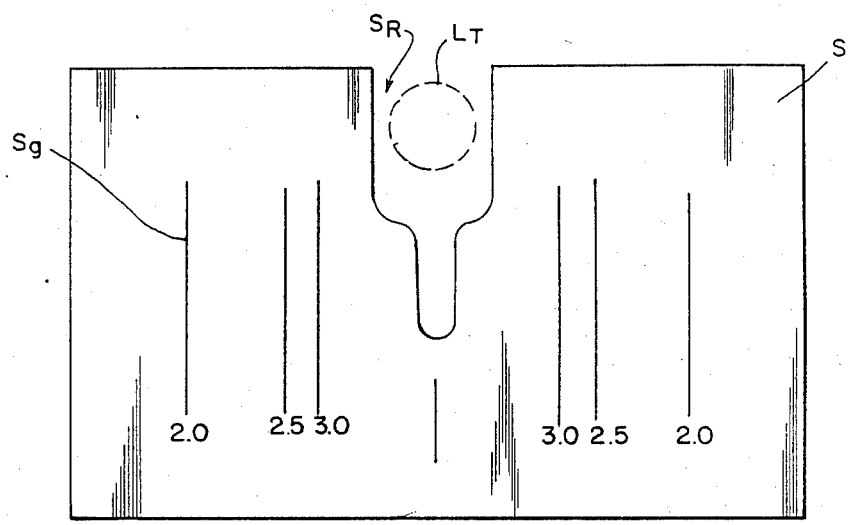
FIG. 4 is a top view of the light screen apparatus of the present invention.

Now referring to FIG. 4 of the drawings, there is shown a top view of the screen S employed in the present invention. As discussed above, the screen S includes a Y-shaped channel Sr for receiving the light transmitting tube $L_T$; it also has on its surface grating indicia Sg for determining the measurement of the muscle tissue's diffraction pattern. The screen S must be made from a translucent material, such as frosted glass, thin fabric, fiberglass, semi-transparent plastic, etc., to enable visual calculation of the diffracted beam on the screen S.

In a preferred mode of use, the screen S is mounted 10 cm. from the top surface (muscle tissue resting surface) of prism P. The muscle tissue sarcomere length can then be determined from the formula $X = \lambda D/S$, where $\lambda = 6.32 \times 10^{-5}$ cm., D = 10 cm. (the distance between the screen S and the muscle bundle 1), S = the sarcomere length in cm., and X = the distance on the screen S between the diffracted and undiffracted beams in cm.

METHOD OF OPERATION Because the objective of any muscle transfer should be the ability of the surgeon to restore the transferred muscle to its resting length
(the resting length of a human skeletal muscle sarcomere is about 2.4μ in the position of function, the length at which myofilament overlap is maximal allowing the muscle to achieve optimal tension levels), the apparatus discussed above is an accurate tool for easily adjusting the resting length of the muscle sarcomere during tendon transfer. Before subjecting muscle fiber to the laser diffraction measurement, a fiber bundle in a muscle must first be dissected free of its fibrous attachment for 3 to 4 cm. along its length using micro instruments, leaving intact all other attachments proximally and distally. Care must be taken to assure that the fibers are not stretched or detached from the bulk of the muscle at either end of the dissection. The resulting bundle should be approximately 1 to 2 mm in thickness. Bundles that are thicker than 2 mm, or those surrounded by their fascia, will not allow the laser beam to pass through and produce a diffraction pattern.

The in vivo muscle fiber bundle is placed on top of the prism, the laser beam directed through both the prism and the muscle fiber bundle, and a clear diffraction pattern is shown on the screen. The screen is desirably calibrated to provide direct measurement of the sarcomere length, according to the formula $X = \lambda D/S$. Thus a sarcomere length of 2.4μ or $2.4 \times 10^{-4}$ cm., leads to a value of 2.63 cm. for X.

It should be understood that the muscle itself acts as a diffraction grating and that this phenomonen along with the geometry of the apparatus gives a magnification on the screen of about 10,000×. Structurally, the present device provides a platform (the prism) which supports the muscle fibers and directs the laser beam into the fiber volume. After light diffraction occurs, the direct and diffracted laser beams travel in air to the detector screen. This construiction enables the device to be used in a "wet", i.e. bloody, environment without losing signficant laser beam intensity. Previous systems do not provide a direct support mechanism for the fiber under examination.

EXAMPLES

The following three examples, taken from the publication of Fleeter, Adams, Brenner and Podolsky, entitiled "A Laser Diffraction Method for Measuring Muscle Sarcomere Length IN VIVO for Application to Tendon Transfers", published in the J. Hand Surgery, 10A, 542, 1985, will illustrate the manner in which the laser diffraction apparatus can be used. It is to be understood that the specific conditions set forth in the examples are not to be considered limiting of the invention, but illustrative only.

EXAMPLE I

Six fresh cadaver forearms were studied (forearm muscle consists largely of parallel longitudinal muscle fiber bundles). On each forearm the extensor digitorum communis (EDS) was isolated, and total muscle length was measured from origin to the musculotendinous junction. The muscles were measured grossly and then examined under the laser diffraction apparatus of the present invention. Each muscle was streched by 10%, 20% and 30%. Sarcomere length measurements showed that the resting length of about 2.4μ was increased proportionally with each increase in total muscle length (see Table I—30% stretch not shown).

Similar studies were carried out on flexor carpi ulnaris (FCU) and palmaris longus (PL) muscles, with similar results (also see Table I—30% stretch not shown for FCU and 20%, 30% stretch not shown for PL).

TABLE I

| Cadaver | Sarcomere Length in Microns | | | | | | Mean % Increase in Sarcomere Length |
|---|---|---|---|---|---|---|---|
| | A | B | C | D | E | F | |
| EXTENSOR *DIGITORUM COMMUNIS* (average rest length 18.7 cm.) | | | | | | | |
| Rest | 2.4 | 2.5 | 2.4 | 2.4 | 2.5 | 2.4 | ↓ |
| +10% (2 cm.) | 2.7 | 2.8 | 2.6 | 2.6 | 2.7 | 2.8 | 11% |
| +20% (4 cm.) | 2.9 | — | 2.8 | 2.9 | 2.8 | 3.0 | 19% |
| *PALMARIS LONGUS* (average rest length 13.5 cm.) | | | | | | | |
| Rest | 2.4 | 2.5 | 2.6 | 2.4 | 2.3 | 2.4 | ↓ |
| +10% (1.5 cm.) | 2.6 | 2.7 | 2.8 | 2.7 | 2.6 | 2.6 | 10% |
| FLEXOR *CARPI ULNARIS* (average rest length 15.5 cm.) | | | | | | | |
| Rest | 2.4 | 2.5 | 2.4 | 2.4 | 2.5 | 2.4 | ↓ |
| +10% (1.5 cm.) | 2.6 | 2.7 | 2.6 | 2.7 | 2.7 | 2.6 | 9% |
| +20% (3 cm.) | 2.9 | 2.8 | 2.8 | — | 2.9 | 2.9 | 17% |

EXAMPLE II

A standard high radial nerve palsy transfer was performed on each of the same cadaver arms used in example I. The FCU was transferred to the EDC tendon, and the PL was transferred to the EPL tendon. After each transfer, sarcomere length measurements were made at the resting total muscle length with the hand in the position of function, and then reset, using the laser diffraction apparatus of the present invention. Each transfer was performed with the hand in the position of funtion, i.e. the wrist at 15° extension; the metacarpal phalangeal joint at 45° flexion, the proximal interphalangeal joint at 30° flexion, and the distal interphalangeal joint at 15° flexion. Resting tension was low enough that after the transfer the position of the hand was unchanged. Transfers made using clinical judgement resulted in attachments in which muscle sarcomere length often was greater than 2.4μ. The use of the laser diffraction apparatus of FIG. 2 allowed precise restoration of the resulting sarcomere length (approximately 2.4μ) after each transfer (see Table II).

TABLE II

| Cadaver | Sarcomere Length in Microns | | | | | |
|---|---|---|---|---|---|---|
| | A | B | C | D | E | F |
| FLEXOR *CARPI ULNARIS* TO EXTENSOR *DIGITORUM COMMUNIS* | | | | | | |
| Rest | 2.4 | 2.5 | 2.4 | 2.4 | 2.5 | 2.4 |
| Clinical | 2.7 | 2.5 | 2.8 | 2.7 | 2.7 | 2.7 |
| Laser | 2.5 | 2.5 | 2.4 | 2.4 | 2.4 | 2.4 |
| *PALMARIS LONGUS* TO | | | | | | |

TABLE II-continued

| Cadaver | Sarcomere Length in Microns | | | | | |
|---|---|---|---|---|---|---|
| | A | B | C | D | E | F |
| EXTENSOR POLLICS LONGUS | | | | | | |
| Rest | 2.4 | 2.5 | 2.4 | 2.4 | 2.5 | 2.4 |
| Clinical | 2.8 | 2.7 | 2.8 | 2.8 | 2.7 | 2.6 |
| Laser | 2.5 | 2.5 | 2.4 | 2.4 | 2.4 | 2.4 |

EXAMPLE III

Utilizing the data obtained from example II, the laser diffraction apparatus of FIG. 2 was used to guide positioning of tendon transfer in two patients with radial nerve palsy (see Table III). The standard set of tendon transfer for high radial nerve palsy was used; FCU to EDC, and PL to EPL. In each case measurements of sarcomere lenght of the PL and FCU were taken first at rest, then after being stretched 10% (using cadaver data for length of the muscle in the position of function—Example II), and a third time after the best clinical judgement was used to position the transfer. It was noted that the 10% stretch increased the sarcomere length by about 10%, confirming measurement made with cadavers.

When clinical judgement was used, the tendency was to overpull the muscle to perform the transfer. The laser diffraction apparatus of FIG. 2 was utilized to identify the excessive stretching of the muscle and correct the resting sarcomere length. Both patients had good control of function six months after surgery.

TABLE III

| | Sarcomere Length in Microns | |
|---|---|---|
| | Patient #1 | Patient #2 |
| FLEXOR CARPI ULNARIS TO EXTENSOR DIGITORUM COMMUNIS | | |
| Rest | 2.4 | 2.4 |
| +10% | 2.7 | 2.6 |
| Clinical | 2.6 | 2.7 |
| Laser | 2.4 | 2.4 |
| POLLICIS LONGUS TO EXTENSOR POLLICIS LONGUS | | |
| Rest | 2.5 | 2.4 |
| +10% | 2.9 | 2.8 |
| Clinical | 2.7 | 2.7 |
| Laser | 2.5 | 2.5 |

It should be understood that the screen S could be replaced with electronic recording means to display via a cathode ray tube screen the resulting diffraction pattern, or provide a digital or analog readout, or a calibrated readout to give sarcomere length directly and the term "screen means" is intended to encompass these variations. Also, that other monochromatic and collimated light sources than a laser can be used, but that some will require modifications and somewhat increase the complexity of the apparatus. It is possible to locate the light source 90° from the support so that a simpler prism (90° reflection) is necessary, but this alteration makes a less convenient appartatus.

It will be obvious to those skilled in the art that various other changes and modifications may be made without departing from the scope of the invention and the invention is not to be considered limited to what is shown in the drawings and described in the specifications.

What is claimed is:

1. A diffraction apparatus for measuring muscle sarcomere length IN VIVO, comprising:
   light soruce means, having a longitudinal axis, for producing a monochromatic and collimated light beam in a direction parallel to said longitudinal axis;
   transparent support means for supporting muscle tissue under examination for measurement of its sarcomere length, said support means being located so that monochromatic light passes therethrough; and
   screen means for receiving light rays diffracted by the muscle tissue after passage through said transparent support means and for providing a magnified measure of the muscle tissue sarcomere length;
   whereby the monochromatic light beam passes through said muscle tissue, diffracting the light beam towards and onto said screen means for determination of said muscle tissue's sarcomere length.

2. An apparatus according to claim 1, wherein said light source means is a laser and said monochromatic light is a laser beam.

3. An apparatus according to claim 2, wherein said transparent support means includes deflection means for deflecting the laser beam 180°, said screen means being mounted normal to said laser means and positioned above said deflection means, said apparatus further comprising means to adjustably position said laser means, said means for transmitting the laser beam from said laser means and said screen means relative to said deflection means.

4. Apparatus according to claim 1, further comprising adjustable positioning means for relative positioning of said light source means, said means for transmitting the monochromatic light beam from said light source means, and said screen means.

5. Apparatus in accordance with claim 3, wherein said support means including said deflection means comprises a prism.

6. Apparatus in accordance with claim 3, wherein said screen means includes a Y-shaped channel for the passage therethrough of said means for transmitting said laser beam from said laser means.

7. Apparatus in accordance with claim 1, wherein said screen means comprises a translucent screen.

8. Apparatus in accordance with claim 3, wherein said screen means comprises a translucent screen.

9. Appartaus in accordance with claim 1, wherein said screen means comprises a screen having grating indicia thereon for measuring sarcomere length.

10. Apparatus in accordance with claim 5, wherein said prism includes shielding means for shielding the incident laser beam from ambient liquids.

11. Apparatus in accordance with claim 3, wherein said means for adjustably positioning said laser means, said means for transmitting said laser beam and said screen means relative to said deflection means, comprises a weight balanced X, Y and Z axial displacement laser supporting device.

12. An apparatus according to claim 1 further comprising transmitting means, coaxial with said longitudinal axis, for transmitting monochromatic light beam from said light source means, said transparent support means being downstream from said transmitting means.

13. A diffraction apparatus for measuring muscle sarcomere length comprising:

light source means, having a longitudinal axis, for producing a monochromatic and collimated light beam in a direction parallel to said longitudinal axis;

transparent support means for supporting muscle tissue under examination for measurement of its sarcomere length, said support means being located so that monochromatic light passes therethrough, said support means including deflection means for deflecting the monochromatic light beam to an angle from said longitudinal axis and through muscle tissue supported on said transparent support means; and screen means for receiving light rays diffracted by the muscle tissue after passage through said transparent support means and for providing a magnified measure of the muscle tissue sarcomere length;

whereby the monochromatic light beam passes through said muscle tissue, diffracting the light beam towards and onto said screen means for the determination of said muscle tissue's sarcomere length.

14. An apparatus according to claim 13, wherein said deflection means comprises means for deflecting the monochromatic light beam 180°.

15. An apparatus according to claim 13, wherein said deflection means comprises a first reflective surface for directing the monochromatic light beam at an angle of about 90° from said longitudinal axis, and a second reflective surface for deflecting the monochromatic light beam another approximately 90° through a muscle supporting surface of said transparent support means and in a direction of about 180° from said longitudinal axis.

16. A diffraction apparatus for measuring muscle sarcomere length in vivo comprising:

light source means, having a longitudinal axis, for producing a monochromatic and collimated light beam in a direction parallel to said longitudinal axis;

transparent support means for supporting muscle tissue under examination for measurement of its sarcomere length, said support means being located so that monochromatic light passes therethrough, said transparent support means including deflection means for deflecting the monochromatic light first 90° from said longitudinal axis and then another 90° to project parallel to said longitudinal axis through a muscle support surface of said support means, said deflection means comprising a prism; and screen means for receiving light rays diffracted by the muscle tissue after passage through said transparent support means and for providing a magnified measure of the muscle tissue sarcomere length;

whereby the monochromatic light beam passes through said muscle tissue, diffracting the light beam towards and onto said screen means for determination of said muscle tissue's sarcomere length.

* * * * *

UNITED STATES PATENT AND TRADEMARK OFFICE
CERTIFICATE OF CORRECTION

PATENT NO. : 4,693,606

DATED : September 15, 1987

INVENTOR(S) : PODOLSKY et al

It is certified that error appears in the above-identified patent and that said Letters Patent is hereby corrected as shown below:

```
Column 2, line  5:  change "come" to read --comere--;
          line 20:  change "sacromere" to read --sarcomere--;

line 56:  delete "the", second occurrence;
Column 3, line  5:  change "sacromere" to --sarcomere--;
Column 7, line 18:  change "lenght" to read --length--;
          line 22:  delete the period "." after "used";
          line 24:  add --the-- before "cadavers";
          line 58:  add --also-- before "possible";
Column 8, line  3:  change "soruce" to read --source--;
          line 18:  add --the-- after "for";
          line 68:  add --in vivo-- after "length";
Column 10, line 28: add --the-- after "for".
```

Signed and Sealed this

Thirtieth Day of May, 1989

Attest:

DONALD J. QUIGG

Attesting Officer

Commissioner of Patents and Trademarks